(12) United States Patent
Waddell (10) Patent No.: US 6,228,090 B1
(45) Date of Patent: May 8, 2001

(54) OSTEOTOMY TRIAL MOUNTING DEVICE AND METHOD

(76) Inventor: David D. Waddell, 2900 Hearne Ave., Shreveport, LA (US) 71103

( * ) Notice: Subject to any disclaimer, the term of this patent is extended or adjusted under 35 U.S.C. 154(b) by 0 days.

(21) Appl. No.: 09/415,194

(22) Filed: Oct. 7, 1999

Related U.S. Application Data (63) Continuation-in-part of application No. 09/210,848, filed on Dec. 15, 1998.

(51) Int. Cl.[7] .................................................... A61B 17/58
(52) U.S. Cl. .................................................. 606/88; 623/18
(58) Field of Search ................................ 606/88, 82, 83, 606/84–87; 623/18–22

(56) References Cited

U.S. PATENT DOCUMENTS

| | | |
|---|---|---|
| 4,633,862 | 1/1987 | Petersen . |
| 5,021,055 | 6/1991 | Buckinshaw et al. . |
| 5,108,401 | 4/1992 | Insall et al. . |
| 5,129,908 | 7/1992 | Petersen . |
| 5,147,365 | 9/1992 | Whitlock et al. . |
| 5,342,367 | 8/1994 | Ferrante et al. . |
| 5,380,332 | 1/1995 | Ferrante . |
| 5,520,692 | 5/1996 | Ferrante . |
| 5,542,947 | 8/1996 | Treacy . |
| 5,690,637 | * 11/1997 | Wen et al. .............................. 606/88 |
| 5,702,464 | * 12/1997 | Lackey et al. .......................... 623/20 |
| 5,720,752 | * 2/1998 | Elliott et al. ........................... 606/88 |
| 5,776,201 | 7/1998 | Colleran et al. . |
| 5,860,980 | 1/1999 | Axelson, Jr. et al. . |

OTHER PUBLICATIONS

Kelly, Michael A., "Patellar Component in Total Knee Arthroplasty," in Current Concepts in Primary and Revision Total Knee Arthroplasty, 1996, pp. 153–158, Lippincott–Raven Publishers, Philadelphia, PA, USA.

Wetzner, Steven M., et al., "Bone Scanning in the Assessment of Patellar Viability Following Knee Replacement," in Clinical Orthopedics and Related Research, No. 119, Oct. 1985, pp. 215–219, USA.

Dorr, Lawrence D., and Richard A. Boiardo, "Technical Considerations in Total Knee Arthroplasty," in Clinical Orthopedics and Related Research, No. 205, Apr. 1986, pp. 5–11, USA.

Brick, Gregory W., and Richard D. Scott, "The Patellofemoral Component of Total Knee Arthroplasty," in Clinical Orthopedics and Related Research, No. 231, Jun. 1988, pp. 163–178, USA.

Aglietti, P., et al., "Patellofemoral Functional Results and Complications With the Posterior Stabilized Total Condylar Knee Prosthesis," in The Journal of Arthroplasty, vol. 3, No. 1, March 1988, pp. 17–25, USA.

Brick, Gregory W., and Richard D. Scott,"Blood Supply to the Patella: Significance in Total Knee Arthroplasty," in The Journal of Arthroplasty, 1989 Supplement, pp. S75–S79, USA.

Ritter, Merrill A., Et Al.,"Patellofemoral Complications Following Total Knee Arthroplasty: Effect of a Lateral Release and Sacrifice of the Superior Lateral Geniculate Artery," in The Journal of Arthroplasty, vol. 11, No. 4, 1996, pp. 368–372, USA.

(List continued on next page.)

*Primary Examiner*—Michael Buiz
*Assistant Examiner*—Lien Ngo (57) ABSTRACT

An osteotomy trial mounting device and method for attaching an osteotomy trial to a surgical tool are provided. The osteotomy trial mounting device includes a trial component, such as a femoral or tibial trial, having a means for attaching a surgical tool. The attachment mechanism includes spaced apart apertures in an attachment surface of the trial for receiving support posts of the surgical tool adapter.

8 Claims, 12 Drawing Sheets

OTHER PUBLICATIONS

Shaw, James A., "A Soft Tissue Closure to Minimize Lateral Patellar Subluxation Following Total Knee Arthroplasty," in American Journal of Knee Surgery, vol. 1, No. 2, Apr. 1986, pp. 112–118, USA.

Insall, James, "Surgical Techniques and Instrumentation in total Knee Arthroplasty," in Surgery of the Knee, $2^{nd}$ Ed., vol. 2, Chapter 26, pp. 767–772.

Superposition of the Patellar Gliding Surface on the Femoral Condyle, p. 15.

* cited by examiner

OSTEOTOMY TRIAL MOUNTING DEVICE AND METHOD

CROSS-REFERENCE TO RELATED APPLICATIONS

This application is a continuation-in-part of U.S. Utility application No. 09/210,848, filed Dec. 15, 1998, entitled "*In Situ Patellar Resection Guide*".

STATEMENT REGARDING FEDERALLY SPONSORED RESEARCH OR DEVELOPMENT

Not Applicable

BACKGROUND OF THE INVENTION

1. Field of the Invention

This invention relates to orthopedic surgical tools, and more particularly, to a system and method for attaching a surgical tool, such as a patellar resection guide, to an osteotomy trial for use in total knee arthroplasty.

2. Description of Related Art Including Information Disclosed under 37 CFR 1.97 and 1.98.

The surgical techniques of total knee arthroplasty are well known in the art. The leading cause of clinical failure of total knee arthroplasty, or total knee revision, is patella problems such as pain and dysfunction of the patella femoral joint. Many patellar failures are related to patellar misalignment with the femoral and tibial replacement components and with the knee extensor mechanism. When the patella fails, it frequently cannot be satisfactorily resurfaced, leading to either removal of its components or a patellectomy. These procedures often result in a major compromise to the functioning of the knee.

Another factor in determining ultimate patellar tracking and prosthesis longevity is accurate placement of the patellar prosthesis in the knee. Its articulation with the femoral groove and femoral component is especially integral to the longevity and success of the prosthesis. In order to maintain an acceptable overall patellar thickness and depth in the femoral groove, appropriate bone removal is a necessity, as well as accurate alignment of the cut bone surface and the patellar component in the sagittal, coronal and transverse planes.

One method popularized as a way to increase patellar prosthesis longevity is lateral retinacular release. Lateral retinacular release is used to improve patella tracking when the prosthesis does not track properly after it has been surgically applied. However, several problems associated with lateral release are well known including increased post-operative hemarthrosis and hematoma. Extensive lateral release also increases the probability of a vascular necrosis due to the sacrifice of the patellar branch of the superior lateral geniculate artery.

For a review of the surgical considerations regarding preparation of the patellar component in total knee arthroplasty, refer to *Patellar Component in Total Knee Arthroplasty*, Kelly, Current Concepts in Primary and Revision Total Knee Arthroplasty, 1996, pages 153–158. Related articles describing the state of the art include the following references: *Bone Scanning in the Assessment of Patellar Viability Following Knee Replacement*, Wetzner, et al, Clinical Orthopedics and Related Research, Number 199, October 1985, pages 215–219; *Technical Considerations in Total Knee Arthroplasty*, Dorr and Boiardo, Clinical Orthopedics and Related Research, Number 205, April 1986, pages 5–11; *The Patellofemoral Component of Total Knee Arthroplasty*, Brick and Scott, Clinical Orthopedics and Related Research, Number 231, June 1988, pages 163–178; *Patellofemoral Functional Results and Complications With the Posterior Stabilized Total Condylar Knee Prosthesis*, Aglietti et al, The Journal of Arthroplasty, Vol. 3, No.1, March 1988, pages 17–25; *Blood Supply to the Patella*, Brick and Scott, The Journal of Arthroplasty, 1989 Supplement, pages S75–S79; *Patellofemoral Complications Following Total Knee Arthroplasty*, Ritter, et al, The Journal of Arthroplasty, Vol. 11, No. 4, 1996, pages 368–372; *A Soft Tissue Closure to Minimize Lateral Patellar Subluxation Following Total Knee Arthroplasty*, Shaw, American Journal of Knee Surgery, Apr. 1986, Vol. 1, No. 2; and *Surgical Techniques and Instrumentation in Total Knee Arthroplasty*, Surgery of the Knee, Insall, James, et al., $2^{nd}$ ed, Vol. 2, Chapter 26, pages 767–772.

The success of surgical techniques in total knee arthroplasty and patellar longevity is also influenced by the tools available to the surgeon. Presently, suitable instrumentation systems and cutting guides for the tibial and femoral components are known in the art. For example, see *Surgical Techniques and Instrumentation in Total Knee Arthroplasty*, Supra, Chapter 26, pages 767–772. These systems and tools have improved surgeons' abilities to implant the components properly and have reduced failures due to improper tibial and femoral condyle component alignment.

There are no known prior art teachings, however, of methods or tools which take into consideration the position of the patella in relation to the femoral condyle at the time of initial patella osteotomy. These cuts are extremely crucial in making sure that the proper relationship of the patella to the femoral groove is maintained and the patellar prosthetic is correctly sited. Instead, most known methods and surgical tools for resection of the patella and resurfacing its posterior surface require extension of the knee and eversion of the patella from its anatomically correct position.

References which discuss subject matter related to patella resection include U.S. Pat. Nos. 5,542,947; 5,520,692; 5,380,332; 5,147,365; 5,129,908; 5,108,401; 5,021,055; and 4,633,862, incorporated herein by reference. Use of the alignment guides, clamps, and surgical saws disclosed in these prior art references for removal of the diseased patellar joint surface and for creating the interface for the patellar component are used with the knee extended, the patella everted, and the extensor and connecting tissue pulled away, so the posterior surface of the patella is exposed.

Although the aforementioned references disclose how a surgeon typically retracts, reshapes, and profiles the patella, these procedures limit a surgeon's ability to accurately align the patellar component in reference to either the femoral or tibial component. When the patella is everted to make the resurfacing cuts, accurate alignment of the patellar surface with the extensor mechanism and articulating surfaces is inordinately difficult.

Figure 12:
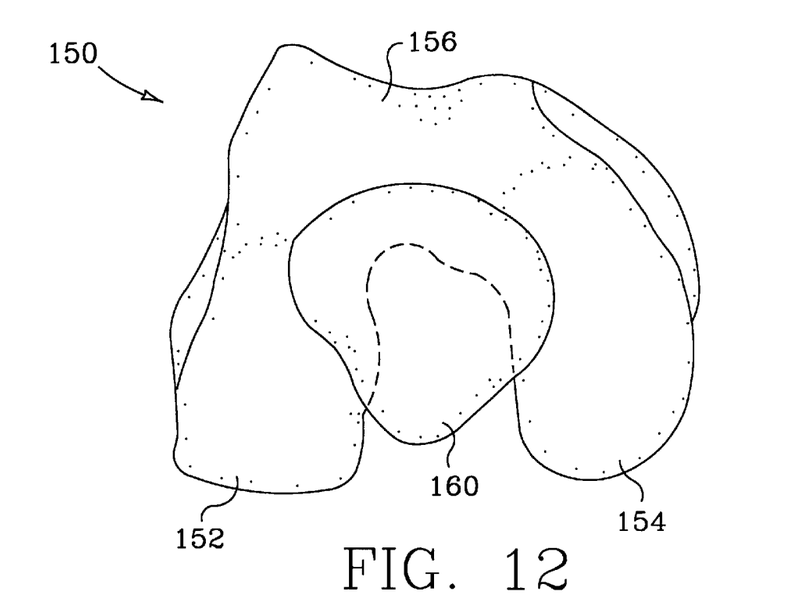
FIG. 12 is a schematic view of a femoral component and patella, depicting the patella's articulation with portions of the femoral condyle in the femorotibial area.
Figure 13:
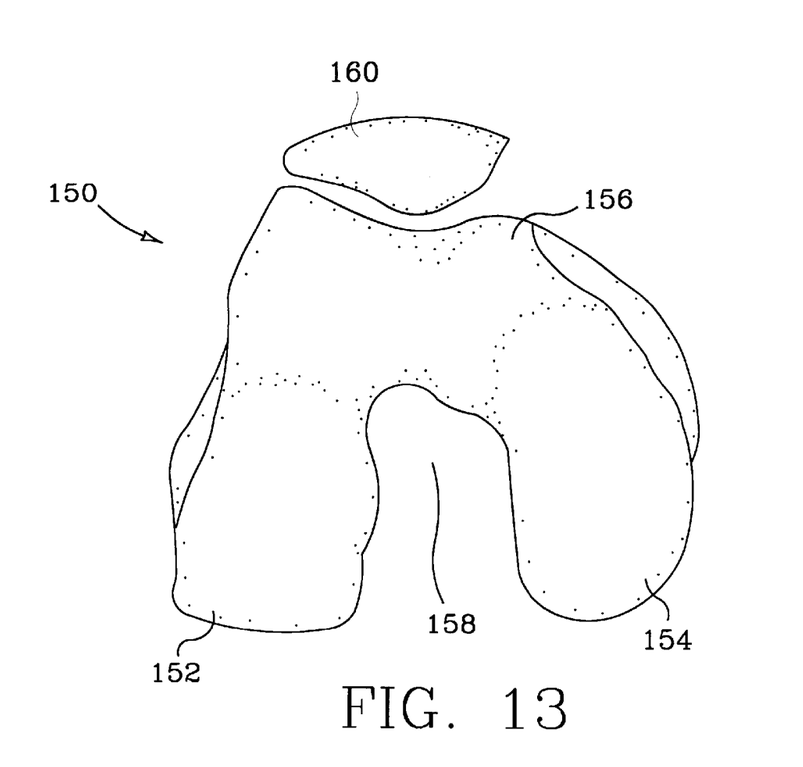
FIG. 13 is a schematic view of a femoral component and patella, depicting the patella's articulation with the femoral patellar surface.

An alternative method of patella resection and resurfacing is disclosed in related U.S. patent application Ser. No. 09/210,848 which permits patella osteotomy while the patella remains in a non-everted, anatomically correct position. Referring to FIGS. 12 and 13, examples of a femoral component 150 depicting anatomically correct positions of the patella 160 in relation to the femoral articulating surfaces are shown. In FIG. 12, the patella 160 is shown adjacent to the femoral condyles 152, 154, where it articulates with portions of the medial 152 and lateral 154 femoral condyles in the true femorotibial area when the knee is in full flexion. When the knee is in extension, the patella 160 articulates solely with the femoropatellar gliding surface 156 as shown in FIG. 13. When the knee is moved between flexion and extion, the patella follows the path of the femoral groove 158. The femoral groove 158 includes the central portion of gliding surface 156 and the space defined between medial and lateral condyles 152, 154.

As disclosed in related U.S. patent application Ser. No. 09/210,848, a tool is now available to surgeons for resurfacing the patella in situ. When mounted directly on a standard metal trial component, such as the femoral trial component of the Hollister-Waddell Total Knee Prosthesis System™, the in situ patellar alignment and cutting guide assists the surgeon in determining the medial/lateral tilt, the superior/inferior cut angle, and resurfacing depth while bringing the patella into an optimum stabilized position before the resectioning is performed. Although the disclosure states that the tool is readily adaptable for use with other total knee systems known in the art, the disclosure does not teach an economical, efficient and safe system or method for using the resection guide with multiple osteotomy trial designs. The present invention meets these needs.

BRIEF SUMMARY OF THE INVENTION

The present invention consists of an osteotomy trial mounting device and method for use with an osteotomy surgical tool such as a patellar resection guide. It is an object of the present invention to provide an osteotomy trial mounting device and method for attaching and using an in situ patellar resection guide with multiple total knee systems and osteotomy trial designs.

In one embodiment of the invention, the device includes a means for attaching a surgical tool to a trial component of a total knee system. The trial component may be either a temporary trial or a traditional metal trial. In a preferred embodiment of the invention, the osteotomy trial may be either a femoral or tibial trial which includes a means for attaching a surgical tool adapter to a patellar resection guide or other alignment and cutting guide.

In one aspect of the present invention, the device includes an osteotomy trial component having a means for attaching the device to a surgical tool. In another aspect, the device includes a surgical tool adapter having support posts which are secured within the surgical tool and the osteotomy trial using locking mechanisms. In one embodiment, the locking mechanism of the surgical tool adapter includes a locking screw for engagement with a threaded aperture on the osteotomy trial.

In a preferred embodiment, the attachment means of the trial component includes two mounting apertures on an attachment surface of the trial which receive the support posts of the surgical tool adapter. In one embodiment, the trial component is a femoral trial having an attachment surface on the medial side, including at least two mounting apertures. In another aspect, the apertures are spaced apart to limit the range of motion of flexion of the human knee during use of the mounted surgical tool. In still another aspect, the placement of the apertures limits the range of motion of flexion of the knee to the range of thirty-five to forty-five degrees.

In another embodiment of the invention, the trial component is manufactured from a plastic material. In one aspect, the material is a high impact plastic. In another aspect, the material is a surgical grade of a disposable material. In yet another aspect, the material is a surgical grade of plastic. In still another aspect, the trial component is manufactured from a reusable, sterilizable material.

The surgical tool adapter includes a means for attaching the surgical tool to a trial component, such as a femoral trial or tibial trial of a total knee system. In one aspect of the present invention, the adapter includes an attachment means for mounting the guide on a femoral component. In another aspect of the invention, the adapter includes an attachment means for mounting the surgical tool on the medial side of the femoral component.

In another aspect of the invention, the attachment means includes two support posts integral with the rear surface of the adapter for insertion into mounting apertures of the trial component.

In another preferred embodiment of the invention, a method of attaching an osteotomy trial of a total knee system to a surgical tool is provided including the steps of identifying the range of motion patterns associated with a specific total knee system to determine a best physiologic range of motion for placement of the surgical tool during use. In one aspect, the method additionally includes the step of adapting the osteotomy trial to include a means for attaching the surgical tool to the trial.

In one aspect of the invention, the step of adapting the trial includes the step of positioning the attachment means to limit the flexion of the human knee to the best physiologic range of motion. In another aspect of the invention, the range of motion of the human knee is limited by the attachment means to thirty-five to forty-five degrees flexion when the device is in use. In still another aspect, the attachment means includes at least two mounting apertures in an attachment surface of the osteotomy trial spaced apart to limit the motion of the human knee to the best physiologic range.

BRIEF DESCRIPTION OF THE SEVERAL VIEWS OF THE DRAWINGS

The invention will be better understood and its numerous objects and advantages will become more apparent to those skilled in the art by reference to the following drawings, in conjunction with the accompanying specification, in which.

DETAILED DESCRIPTION OF THE INVENTION

Figure 1:
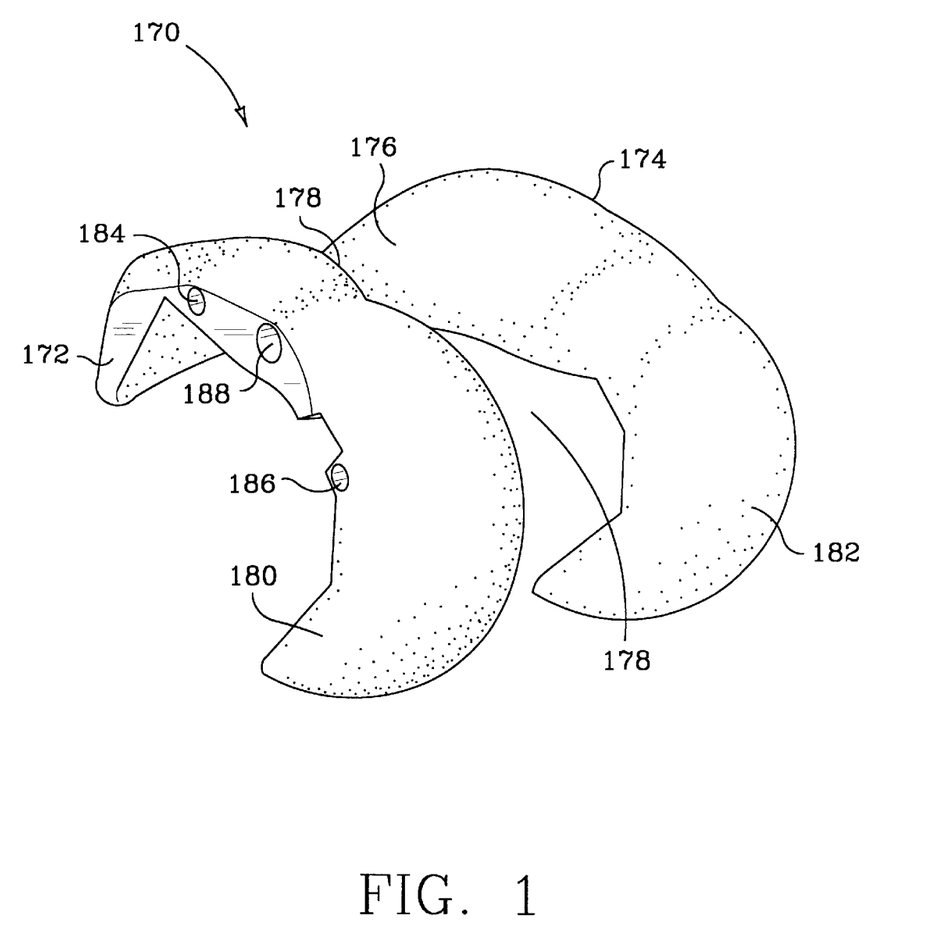
FIG. 1 is a medial-posterior perspective view of an embodiment of an osteotomy trial component of the present invention.
Figure 2:
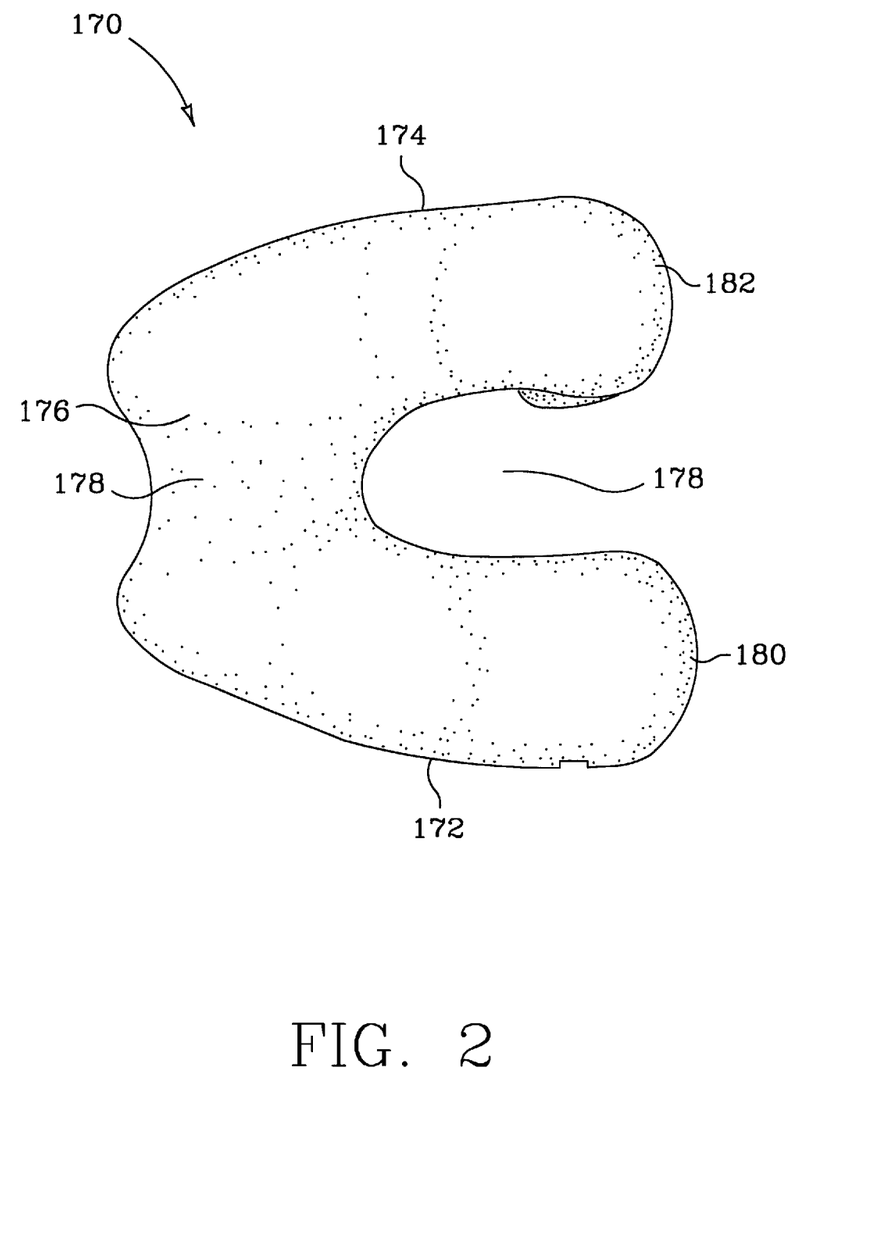
FIG. 2 is a top plan view of the osteotomy trial shown in FIG. 1.
Figure 3:
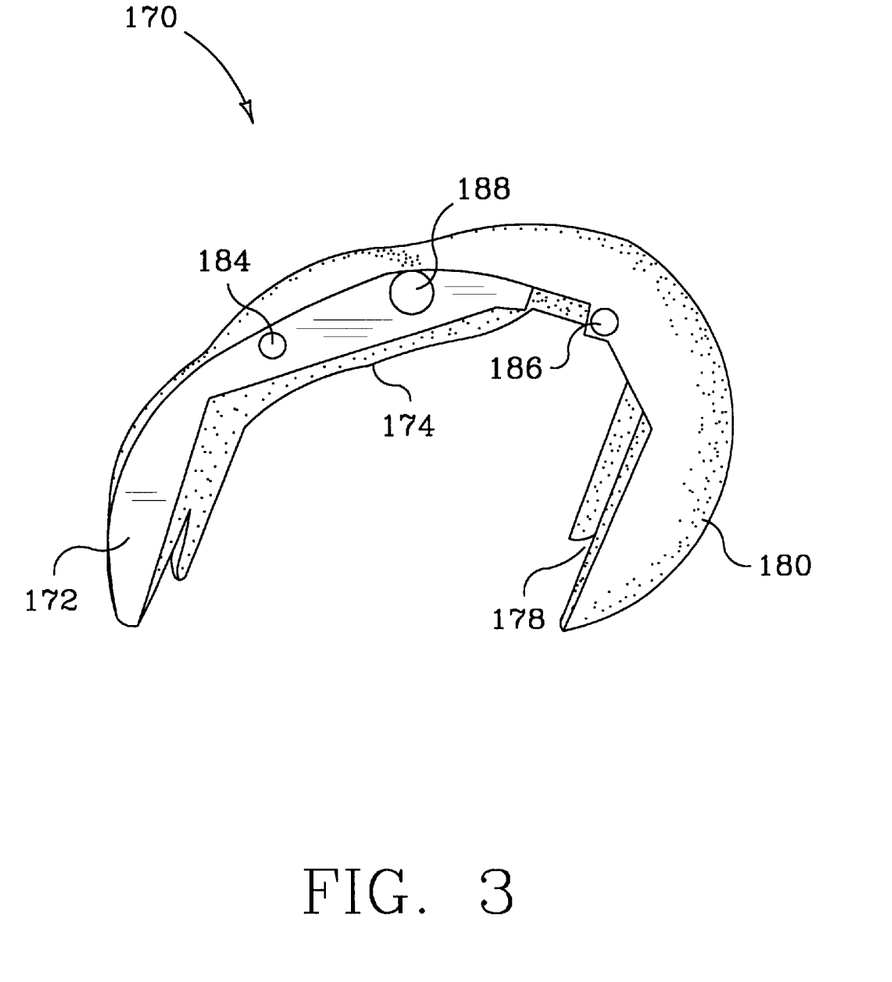
FIG. 3 is a medial side view of the osteotomy trial shown in FIG. 1.

An osteotomy trial mounting device and method for attaching an osteotomy trial to a surgical tool are disclosed. Referring to FIGS. 1–3, a preferred embodiment of an osteotomy trial component 170 having a means for attaching a surgical tool is shown. Specifically, osteotomy trial component 170 is a left knee femoral trial having a medial side 172, lateral side 174, anterior articulating surface 176, medial and lateral spaced apart condyles 180, 182 and femoral groove 178 extending from the central portion of articulating surface 176 through the space between the medial and lateral condyles 180, 182.

Femoral trial 170 is depicted having the length of the medial side 172 as an attachment surface 172. In the preferred embodiment, attachment surface 172 includes at least two mounting apertures 184 and 186 spaced apart to limit the range of flexion of the human knee once the surgical tool is mounted on the trial 170 and the trial component 170 is installed on the human knee for use during total knee surgery. Specifically, mounting aperture 184 is proximal to the articulating surface 176, whereas mounting aperture 186 is distally located from aperture 184 and anterior surface 176 near the medial condyle 180.

Figure 4:
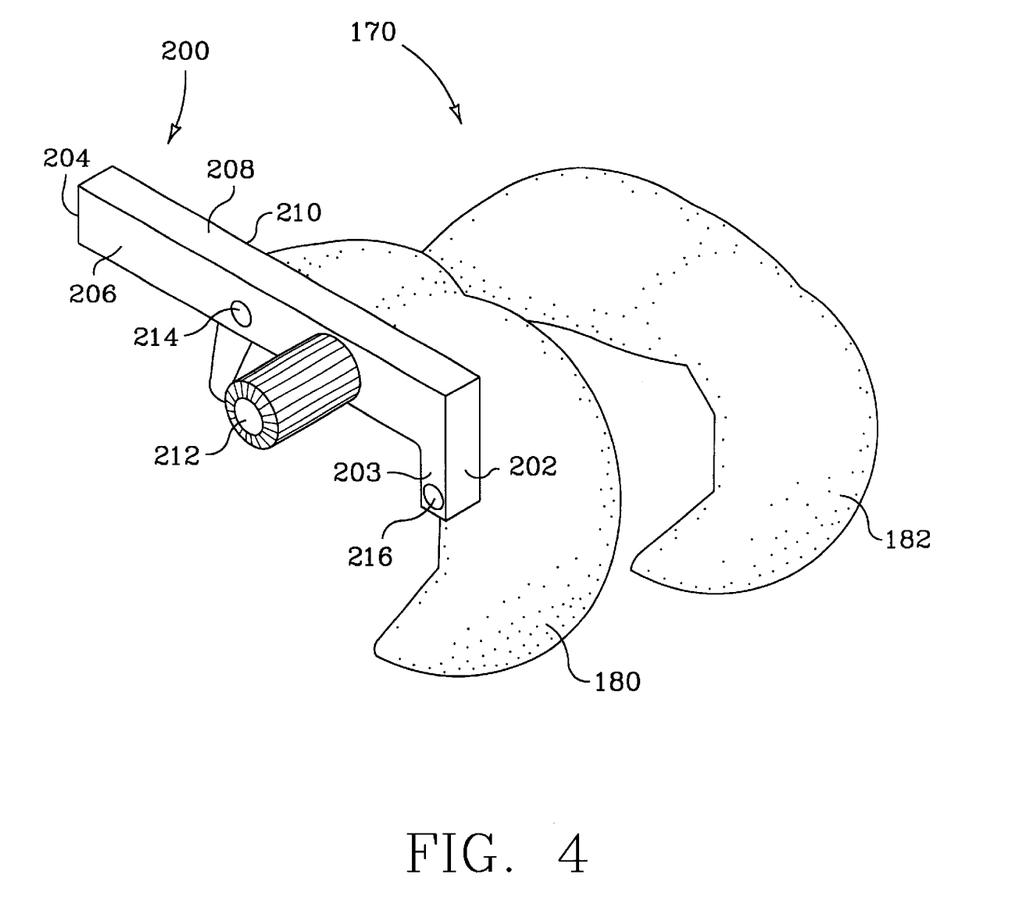
FIG. 4 is a medial-posterior perspective view of an embodiment of the osteotomy trial mounting device of the present invention depicting an osteotomy trial attached to a left knee surgical tool adapter.
Figure 5:
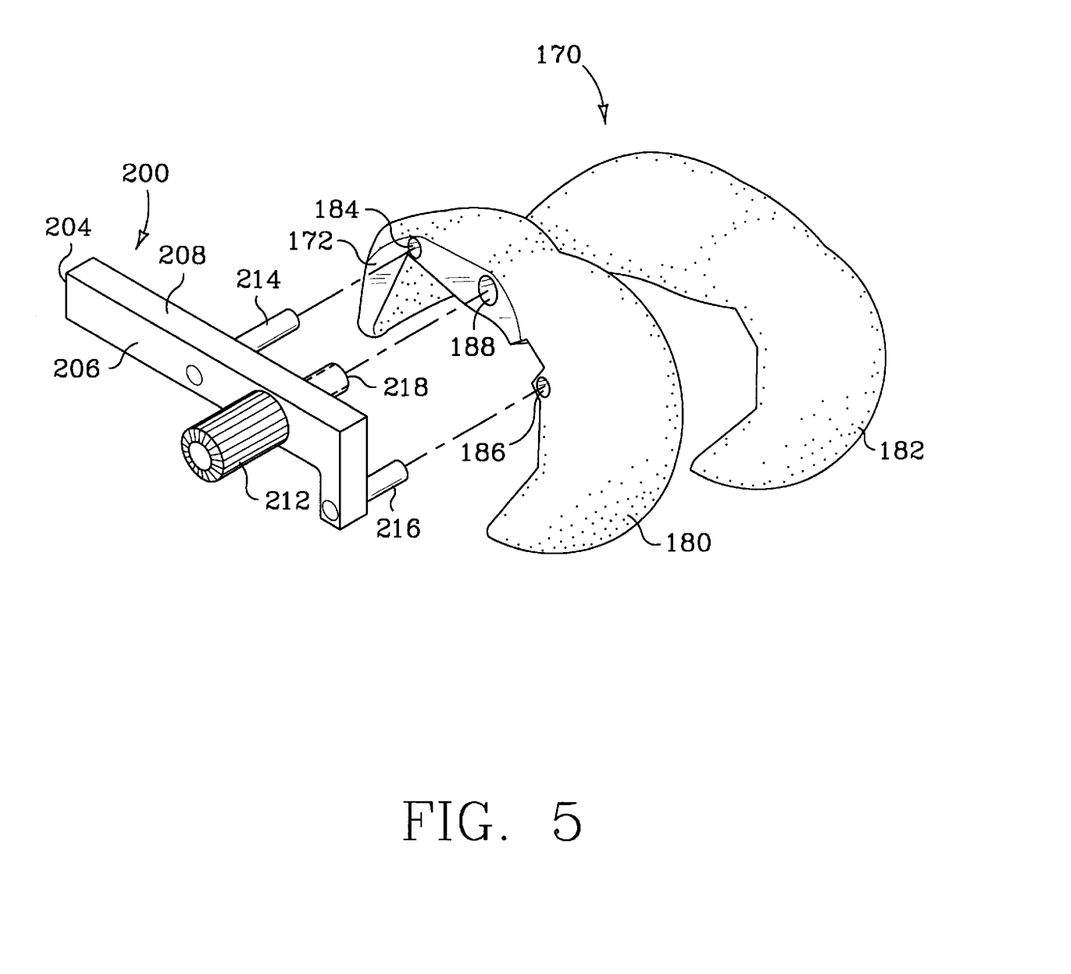
FIG. 5 is an exploded medial-posterior perspective view of the osteotomy trial mounting device shown in FIG. 4.

In its preferred embodiment, mountable osteotomy trial 170 is secured to a surgical tool using a surgical tool adapter such as adapter 200 shown in FIGS. 4 and 5. Referring to FIGS. 4 and 5, the osteotomy trial mounting device of the present invention is shown to include a left knee femoral component 170 and surgical tool adapter 200. Surgical tool adapter 200 includes a right side 202, flange 203, left side 204, a front face 206, a tool attachment surface 208, and a trial attachment surface 210 having a means for attaching the adapter 200 to a mountable trial component. In the embodiment shown, the attachment means includes trial engagement posts 214, 216 for insertion in mounting apertures 184, 186 of femoral trial component 170.

Surgical tool adapter 200 additionally includes a locking mechanism 212 having a post 218 for insertion into locking aperture 188 of trial component 170. In a preferred embodiment, locking post 218 and aperture 188 are threaded for immovably securing the trial to the adapter during use of the surgical tool (not shown). In the embodiment shown, aperture 188 and post 218 serve the additional function of a third mounting aperture. The precise position of aperture 188 and post 218 between mounting apertures 184, 186 and posts 214, 216 may also be used to limit the range of flexion of the human knee during use of the attached surgical tool.

It will be understood and appreciated by those skilled in the art that the mountable trial component need not be limited to the femoral trial. The component may be an alternative component of the total knee system, such as a tibial trial component (not shown) with the surgical tool mounted on either the lateral or medial side, near the tibial plateau. Using the disclosure and teachings of the present invention, one skilled in the art may determine the best location for machining or manufacturing a mountable tibial trial which limits the risk of harm to the tendons of the human joint while using the osteotomy tools, saws and resurfacing devices.

The osteotomy trial mounting device may be a disposable device manufactured of a surgical grade of plastic material, a sterilizable, reusable device, or a modified traditional metal trial. When manufactured of a high impact plastic, the trial components of the invention are suitable, economic alternatives to the use of metal trials currently included in total knee prosthetic systems. For example, the present invention enables the surgeon to make the necessary cuts and resections using a surgical tool mounted on the trial of the invention. Once the cuts are made, the mountable trial may be removed from the human knee and replaced with the traditional metal trial for the final tests before installation of the prosthetic component. If manufactured of a high impact plastic, the mountable trial may remain in place for the final tests after the surgical tool is unmounted, dispensing with the need for testing the total knee system with the metal trial before installation of the prosthetic component.

An essential element of the invention is the spaced apart relationship of the mounting apertures 184, 186, 188 on trial component 170 and the placement of corresponding support posts 214, 216, 218 on tool adapter 200. Precise placement of apertures 184, 186, 188 with respect to the posts 214, 216, 218 of the adapter 200 is necessary to maintain knee stability and safety of the surrounding tissues and tendons during use of a mounted surgical tool. In addition, the number, position and rotational orientation of apertures in the trial component as well as the number and placement of the corresponding support posts on the tool adapter further control the angles of cuts available to the surgeon, removing much of the uncertainties and risks often associated with total knee surgery.

Figure 6:
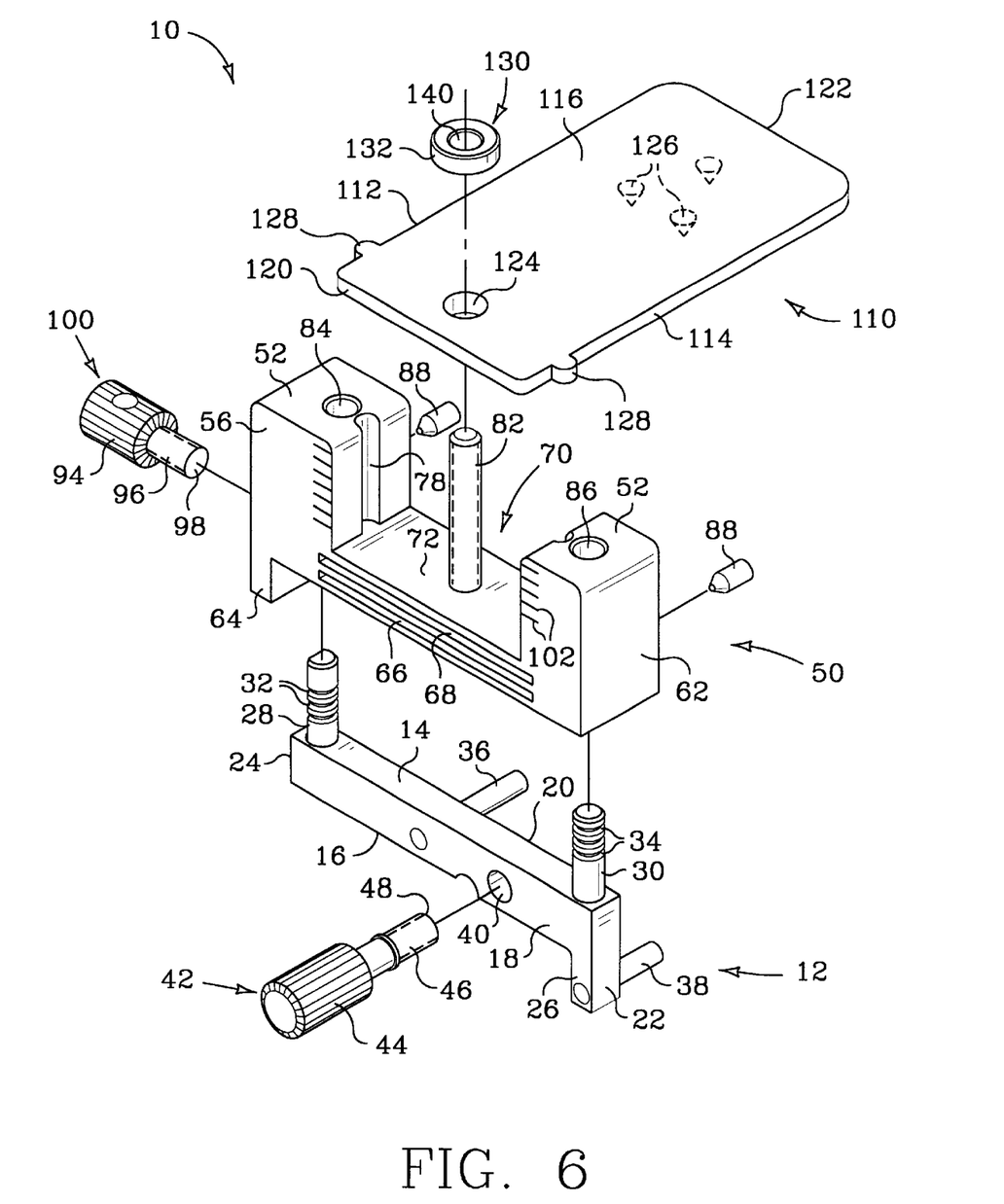
FIG. 6 is an exploded right front perspective view of an example surgical tool adapted for use with the osteotomy trial of the present invention.
Figure 10:
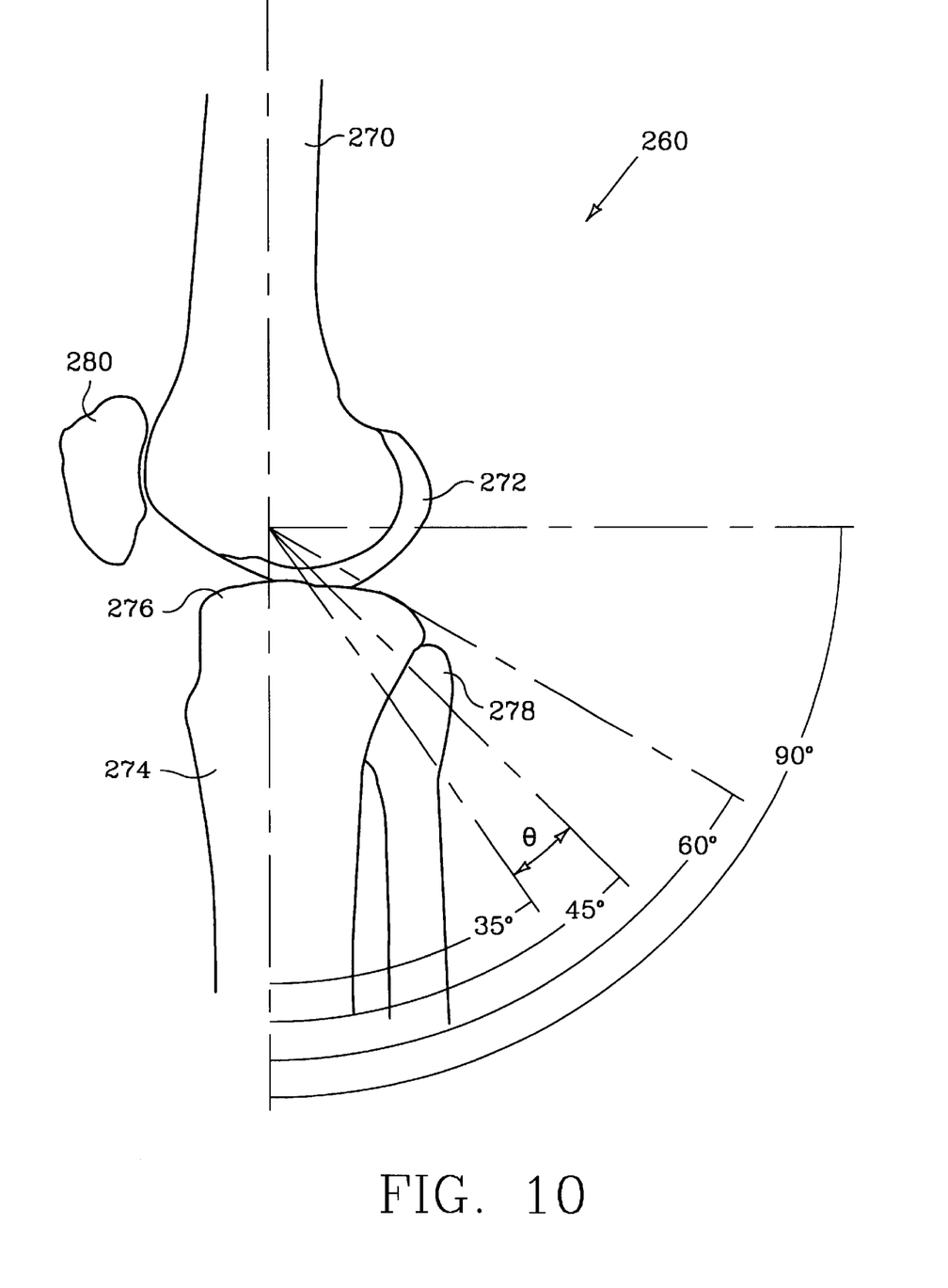
FIG. 10 is a schematic lateral side elevation view of the left anatomical human knee showing the range of flexion of the knee from zero to ninety degrees.
Figure 11:
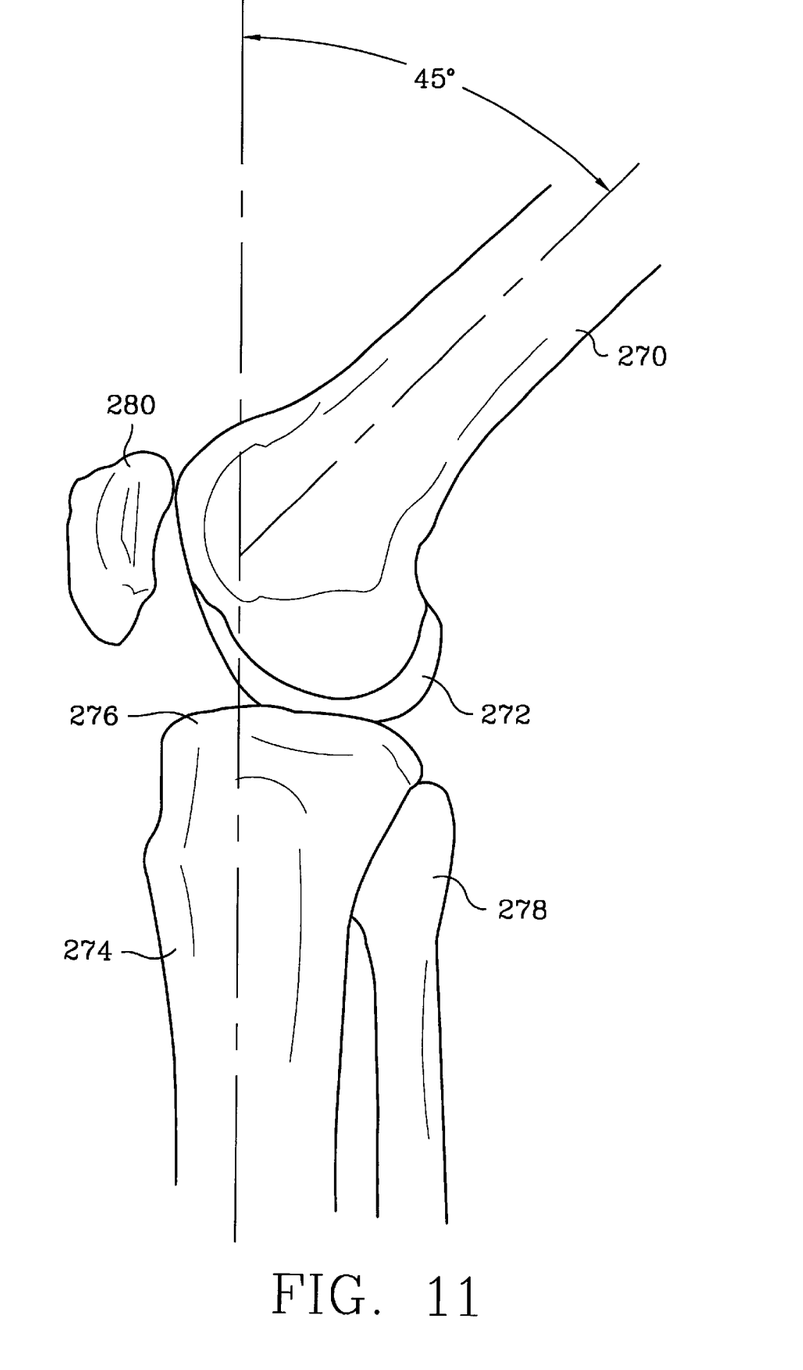
FIG. 11 is a schematic lateral side elevation view of the left anatomical human knee showing the preferred flexion point of the knee at forty-five degrees for use with the osteotomy trial mounting device of the present invention.

Through an iterative process utilizing the in situ patella resection guide shown in FIG. 6 and a femoral trial component 170, it was discovered that the knee should be flexed within the range of thirty-five to forty-five degrees for safe in situ patella resectioning when using a mounted surgical tool. Referring to FIGS. 10 and 11, a schematic lateral side elevation view of the left anatomical human knee is depicted, showing the range of flexion of the knee from zero to ninety degrees. The diagrams of FIGS. 10–11 show a left human knee 260 including the femur 270, lateral condyle 272, tibula 274, tibular plateau 276, fibula 278 and patella 280. Maintaining the knee in the preferred range of flexion, identified as angle $\theta$ from 35°–45°, helps keep the quadriceps tendon out of the potential of harm from the osteotomy saw and other tools. Extreme care must be taken by the surgeon to not damage the tendons if cuts are made using a mounted tool which permits flexion outside of the preferred range. Limitation to the preferred range disclosed herein drastically reduces the risk of harm, thereby increasing the safety of the invention and the invention disclosed in the parent application.

Figure 7:
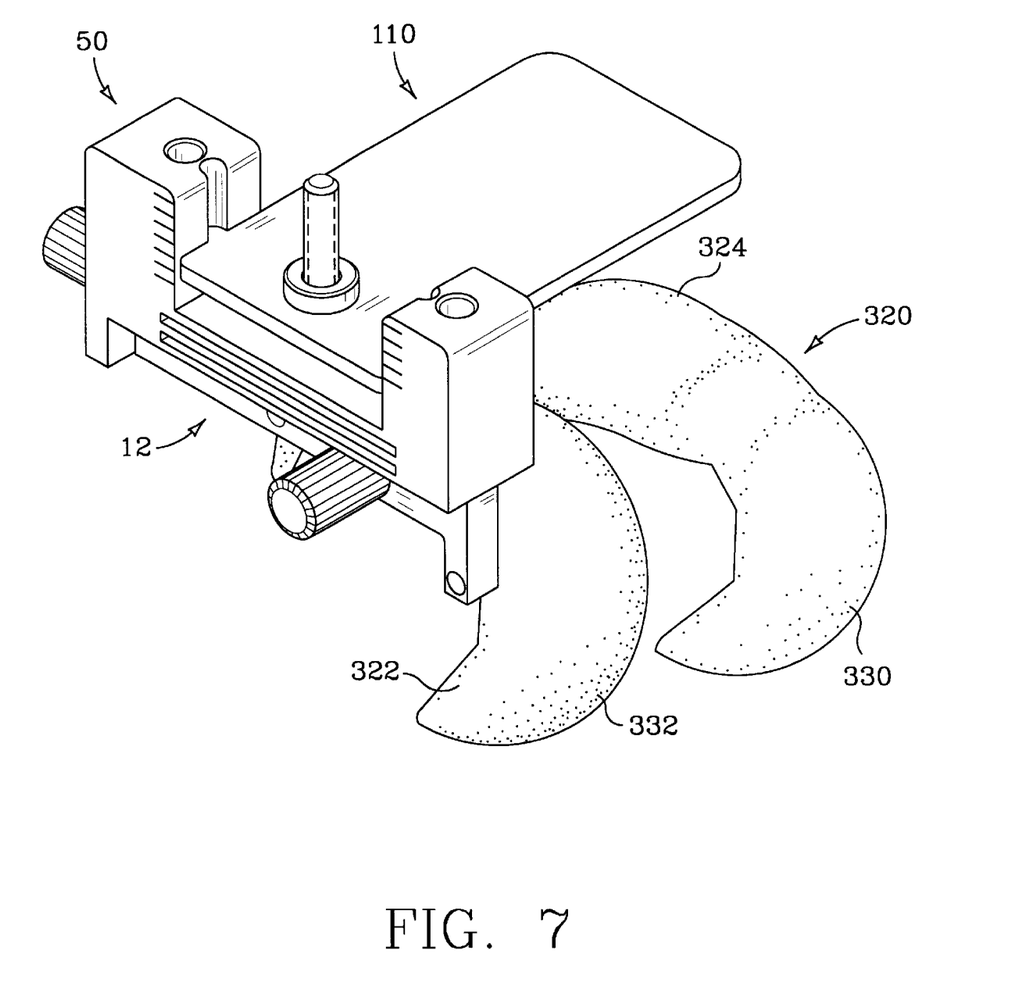
FIG. 7 is a right front perspective view of the surgical tool shown in FIG. 6, mounted on the medial side of a femoral trial of the present invention using a left knee surgical tool adapter.
Figure 8:
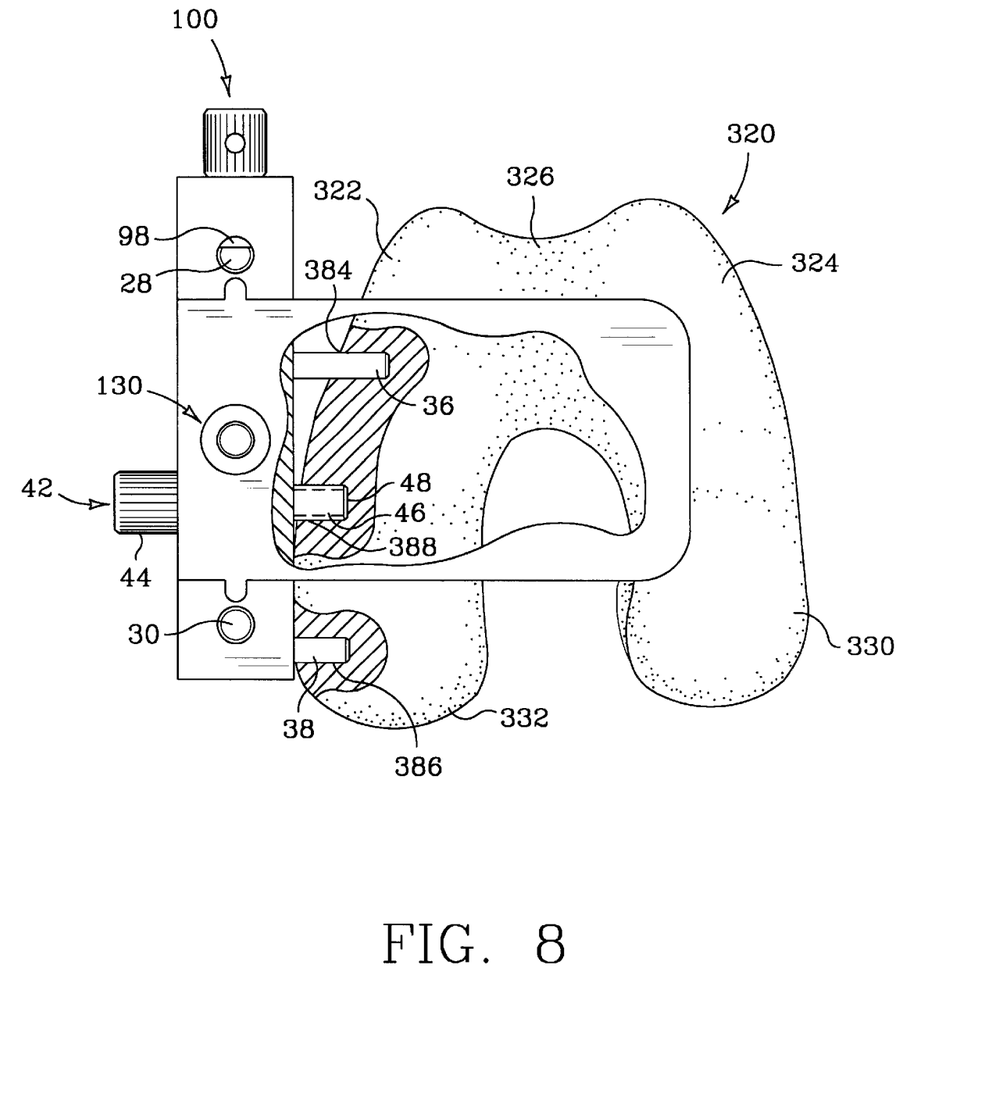
FIG. 8 is a top view of the surgical tool and mountable osteotomy trial shown in FIG. 7 partially cutaway.

Referring to FIGS. 6–8, a mountable trial component 320 device of the invention is shown attached to an in situ patellar resection guide 10 by way of example. With reference to FIG. 6, the patellar alignment and cutting guide 10 includes a patellar plate 110, slotted block 50 and surgical tool adapter 12. As taught in U.S. parent application Ser. No. 09/210,848, guide 10 permits the surgeon to use the improved technique of resurfacing a human patella while in a normal anatomic position during a total knee arthroplasty.

In summary, slotted block 50 of the resection guide 10 includes a top 52, bottom 54, left face 56, right face 58, first side 60, second side 62, flange 64, horizontal slots 66, 68, vertical bores 84, 86, apertures 90, calibration markings 102, and a plate retaining window 70. The plate retaining window 70 further comprises a horizontal interior surface 72, interior walls 74, 76, channels 78, 80, and a plate retaining post 82. Patellar plate 110 of the invention includes sides 112, 114, upper surface 116, lower surface 118, front end 120, rear end 122, aperture 124, gripping means 126, and tabs 128. The details of the in situ patella resection guide are disclosed in U.S. parent application Ser. No. 09/210,848, herein incorporated by reference.

The mounting position of guide 10 on a trial knee component such as left knee femoral trial component 320 as shown is controlled by the precise placement of apertures 384, 386, in medial attachment surface 322 and the placement of corresponding support posts 36, 38 of surgical tool adapter 12. Trail component 320 includes medial attachment surface 322, lateral surface 324, anterior articulation surface 326 and posterior condyles 330, 332.

The surgical tool adapter 12 shown in FIGS. 6–8 is for use with a left knee component and includes an upper tool attachment surface 14, lower surface 16, a front surface 18, a trial component attachment surface 20, a right side 22, a left side 24, and a flange 26. In this embodiment, the means for attaching the adapter to the patellar resectioning tool is shown as two grooved posts 28, 30, having grooves 32, 34, adjacent to attachment surface 14. The tool adapter 12 is optionally secured to femoral trial 320 using a locking screw 42, inserted within locking mounting aperture 388. Locking screw 42 includes a knob 44 adjacent to the front surface 18 of base 12, shaft 46, and end 48.

Figure 9:
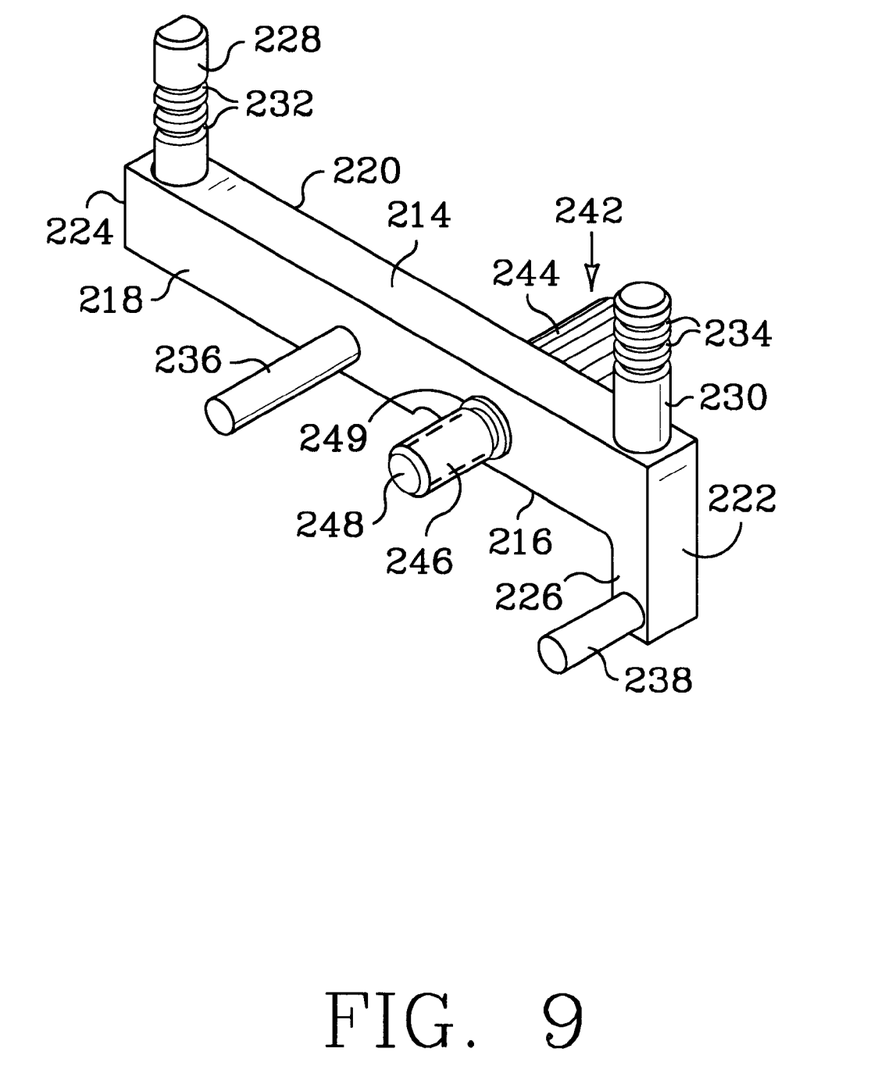
FIG. 9 is a right front perspective view of a right knee surgical tool adapter of the present invention.

Alternatively, the adapter base 212 of FIG. 9 may be used with a right knee mountable trial component and includes a tool attachment surface 214 having grooved posts 228, 230, a lower surface 216, a trial component attachment surface 218, a front surface 220, a right side 222, a left side 224, and a flange 226. In this embodiment, the attachment means includes support posts 236, 238 and locking mechanism 242 having a knob 244, shaft 246, end 248 and washer or flange 249 for engagement with a locking aperture on the trial component such as aperture 188 of trial 170 or aperture 388 of trial 330.

Using a tool adapter such as adapter 12 or 212, the guide 10 is mounted directly on the mountable femoral trial component and attached to the femur site of the human knee. This firm fixation onto a trial component ensures proper alignment of the patella with the other components, and allows proper patella angle, patella cut angle, and depth of cut.

In the method of the invention, the range of motion patterns associated with a specific total knee system are identified to determine a best physiologic range of motion for placement of a mountable surgical tool during use. Next, the osteotomy trial of the total knee system, such as the metal femoral or tibial trial, is modified to include a means for attaching a surgical tool. This step includes the step of positioning the attachment means to limit the flexion of the human joint or knee to the best physiologic range of motion for optimum safety during use of the mounted tool. The step of positioning the attachment means includes drilling at least one aperture in the attachment surface of the mountable trial for receiving a support post of a surgical tool adapter. Alternatively, the step of positioning the attachment means may include manufacturing a mountable trial having at least one aperture in its attachment surface.

It will be understood and appreciated by those skilled in the art using the teachings of this invention, that the mountable osteotomy trial device, of the present invention including the surgical tool adapter can be modified for use with multiple total knee systems and osteotomy tools. As disclosed above, modification of the invention for additional embodiments includes shifting the apertures and support posts to accommodate the different arcs of motion of the alternative trial component and other tools commonly utilized for knee reconstruction surgery. The drawings and foregoing description are provided by way of example and not for the purpose of limitation, the scope of the invention being delineated in the following claims.

I claim:

1. An osteotomy trial mounting device for use during a total knee arthroplasty on a human knee, to attach a surgical tool to a trial component, comprising:

an osteotomy trial component having an attachment surface with two mounting apertures and a locking aperture, wherein the locking aperature and the two mounting apertures are spaced apart to limit flexion of the human knee in a range of thirty-five to forty-five degrees when the surgical tool is in use; and a surgical tool adapter having a trial component attachment mechanism including two trial support posts and one locking mechanism with a stabilizing post;

wherein said trial support posts are received within said mounting apertures and said stabilizing post is received within said locking aperture.

2. The osteotomy trial mounting device of claim 1, wherein the surgical tool is an in situ patella resection guide.

3. The osteotomy trial mounting device of claim 1, wherein the osteotomy trial is a femoral trial.

4. The osteotomy trial mounting device of claim 3, wherein the attachment surface is the medial side of the femoral trial.

5. The osteotomy trial mounting device of claim 1, wherein the osteotomy trial is plastic.

6. The osteotomy trial mounting device of claim 5, wherein the plastic osteotomy trial is reusable.

7. The osteotomy trial mounting device of claim 5, wherein the osteotomy trial is a high impact, surgical grade of plastic.

8. A method of attaching an osteotomy trial of a total knee system to a surgical tool, comprising the steps of:

identifying the range of motion patterns associated with a specific total knee system to determine a best physiologic range of motion for placement of said surgical tool during use;

adapting the osteotomy trial of said total knee system to include an attachment surface having two mounting apertures and a locking aperture spaced apart to limit flexion of the human knee in the range of thirty-five to forty-five degrees when attached to said surgical tool; and modifying a surgical tool adapter having two trial support posts and one locking mechanism with a stabilizing post such that said posts cooperatively engage with the spaced apart locking aperture and mounting apertures of the adapted osteotomy trial.

* * * * *

UNITED STATES PATENT AND TRADEMARK OFFICE
CERTIFICATE OF CORRECTION

PATENT NO.     : 6,228,090 B1
DATED          : May 8, 2001
INVENTOR(S)    : David D. Waddell

It is certified that error appears in the above-identified patent and that said Letters Patent is hereby corrected as shown below:

<u>Column 1,</u>
Line 12, in the STATEMENT REGARDING FEDERALLY FUNDED RESEARCH OR DEVELOPMENT, please delete "Not Applicable" and replace with:

-- This invention was made with Government support under contract number DE-FG02-96ER62280 awarded by the Department of Energy. The Government has certain rights in this invention. --

Signed and Sealed this

Fifteenth Day of July, 2003

JAMES E. ROGAN
*Director of the United States Patent and Trademark Office*